United States Patent [19]

Hamilton

[11] Patent Number: 5,510,338
[45] Date of Patent: Apr. 23, 1996

[54] PHOSPHONOALKYLQUINOLIN-2-ONES AS NOVEL ANTAGONISTS OF NON-NMDA IONOTROPIC EXCITATORY AMINO ACID RECEPTORS

[75] Inventor: Gregory S. Hamilton, Catonsville, Md.

[73] Assignee: Guilford Pharmaceuticals Inc., Baltimore, Md.

[21] Appl. No.: 260,239

[22] Filed: Jun. 14, 1994

Related U.S. Application Data

[62] Division of Ser. No. 984,453, Dec. 2, 1992, Pat. No. 5,342,946.

[51] Int. Cl.$^6$ .................... C07D 215/227; C07D 215/18; C07D 215/38; A61K 31/47
[52] U.S. Cl. ................... 514/82; 546/21; 546/23
[58] Field of Search .......................... 546/21, 23; 514/82

[56] References Cited

U.S. PATENT DOCUMENTS

| | | | |
|---|---|---|---|
| 4,657,899 | 4/1987 | Rzeszotarski et al. | 514/120 |
| 4,761,405 | 8/1988 | Rzeszotarski et al. | 514/114 |
| 4,822,780 | 4/1989 | Tsuda et al. | 514/119 |
| 4,918,064 | 4/1990 | Cordi et al. | 514/114 |
| 5,049,555 | 9/1991 | Rzeszotarski et al. | 514/114 |
| 5,217,963 | 6/1993 | Hutchison | 514/82 |

FOREIGN PATENT DOCUMENTS 432994  6/1991  European Pat. Off. .

OTHER PUBLICATIONS

Hamilton, *Bioorganic & Medicinal Chemistry Letters*, vol. 2 No. 10, pp. 1269–1274, 1992.
Hamilton, *Bioorganic & Medicinal Chemistry Letters*, vol. 4 No. 16, pp. 2035–2040, 1994.
Watkins et al., "Excitatory Amino Acid Transmitters," *Amer. Rev. Pharmacol. Toxicol.* (1981), vol. 21, pp. 165–204.
Schwarcz et al., "Quinolinic Acid: An Endogenous Metabolite that Produces Axon–Sparing Lesions in Rat Brain," *Science*, Jan. 1983, vol. 219, pp. 316–318.
Simon et al., "Blockade of N–Methyl–D–Aspartate Receptors May Protect Against Ischemic Damage in the Brain," *Science*, vol. 226, pp. 850–852, 1984.
Foster et al., "Acidic Amino Acid Binding Sites in Mammalian Neuronal Membranes: Their Characteristics and Relationship to Synaptic Receptors," *Brain Research Reviews*, vol. 7, (1984), pp. 103–164.
Schoepp et al., "Pharmacological and Functional Characteristics of Metabotropic Excitatory Amino Acid Receptors," *Tr. Pharmacol. Sci.*, Special Report (1991), pp. 74–81.
Faden et al., "Effects of Competitive and Non–Competitive NMDA Receptor Antagonists in Spinal Cord Injury," *European Journal of Pharmacology*, vol. 175 (1990), pp. 165–174.

Frandsen et al., "Direct Evidence that Excitotoxicity in Cultured Neurons is Mediated via N–Methyl–D–Aspartate (NMDA) as well as Non–NMDA Receptors," *Journal of Neuro–Chemistry*, vol. 53, No. 1, 1989, pp. 297–299.
Sheardown et al., "2,3–Dihydroxy–6–nitro–7–sulfamoyl–benzo(F)quinoxaline: A Neuroprotectant for Cerebral Ischemia," *Science*, vol. 247, Feb. 1990, pp. 571–574.
Costa, "Allosteric Modulatory Centers of Transmitter Amino Acid Receptors," *Neuropsychopharmacology*, vol. 2, No. 3, (1989), pp. 167–174.
Matoba et al., "Structural Modification of Bioactive Compounds. II. Syntheses of Aminophosphonic Acid," *Chem. Pharm. Bulletin*, vol. 32 (1984, pp. 3918–3925.
Lodge et al., [Eds.], "The Pharmacology of Excitatory Amino Acids," *Elsevier Trends Journal* (1991).
Stuart Smith, "The non–N–methyl–d–aspartate Receptor . . . ", *European Journal of Pharmacology*, 201, 1991, pp. 179–183.
Smith, "Cerebroprotective Effect . . . ", *Stroke*, vol. 23, pp. 861–864, 1992.
Gill, "The Neuroportective . . . ", *Europharmacology*, vol. 33, No. 12, pp. 1529–1536, 1994.
Judge, "protection Against . . . ", *Neuroscience Letters*, vol. 133, pp. 291–294, 1991.
Krogsgaard–Larsen, "Novel Class of Amino . . . ", *J Med Chem*, vol. 34, pp. 123–130, 1991.
Peillet, "The non–NMDA . . . ", *Brain Research*, vol. 571, pp. 115–120, 1992.
Wong, "Sites for Antagonism . . . ", *Annu. Rev. Pharmacol. Toxicol.*, vol. 31, pp. 401–425, 1991.
M. Regitz, *Tetrahedron Letters*, vol. 38, pp. 3979–3982, 1972.

Primary Examiner—C. Warren Ivy
Assistant Examiner—D. Margaret M. Mach
Attorney, Agent, or Firm—Nath & Associates; Gary M. Nath; Suet M. Chong

[57] ABSTRACT

The present invention pertains to antagonists of excitatory amino acid receptors, their method of preparation as well as compositions pertaining to them, which have the general formula:

[Structure: quinolin-2-one with $R_2$ substituent, $R_1$ substituent, and $(CH_2)_n PO_3 H_2$ group]

wherein n is 0, 1, 2, or 3; R1 and R$_2$ are selected from the group consisting of hydrogen, halogen, halomethyl, nitro, amino, alkoxy, hydroxyl, hydroxymethyl, $C_1$ to $C_6$ lower alkyl and $C_7$ to $C_{12}$ higher alkyl, aryl and aralkyl; and the pharmaceutically acceptable salts thereof.

6 Claims, No Drawings

PHOSPHONOALKYLQUINOLIN-2-ONES AS NOVEL ANTAGONISTS OF NON-NMDA IONOTROPIC EXCITATORY AMINO ACID RECEPTORS

This application is a division of U.S. patent application Ser. No. 07/984,453, filed Dec. 2, 1992, now U.S. Pat. No. 5,342,946, the entire contents of which are incorporated herein in their entirety.

BACKGROUND OF THE INVENTION

1. Field of the Invention

The present invention pertains to novel non-N-methyl-D-aspartate excitatory amino acid (EAA) receptor antagonists and particularly to novel, potent and selective antagonists of kainic acid (KA) and AMPA [ (R,S)-α-aminomethyl-3-hydroxy-5-methylisoxazole propionic acid]type receptors having anxiolytic, anticonvulsant, antiepileptic, analgesic, antiemetic, neuroprotective and cognition enhancing actions achieved through the antagonism of these receptors. In particular, the invention is directed to: substituted 4-phosphonoalkylquinolin-2-ones and their interaction with KA and AMPA receptors, their pharmaceutically acceptable salts, and to uses thereof.

2. Description of the Prior Art

Excitatory amino acids (EAAs) mediate a substantial portion of the neurochemical synaptic activity occurring in the central nervous system. Current understanding recognizes at least three major ionotropic receptors for EAAs. Most commonly identified by prototypical agonists, these include:

(1) receptors activated by AMPA [(R,S)-α-aminomethyl3-hydroxy-methylisoxazole propionic acid], a cyclic analog of L-glutamate (GLU), (2) receptors recognizing the pyrrolidine neurotoxin kainic acid (KA), and three receptors responding to N-methyl-D-aspartate (NMDA), a synthetic analog of L-aspartate [D. R. Curtis, A. W. Duggar, D. Felix, G. A. R. Johnston, A. K. Tebecis and J. C. Watkins, Brain Res., 41, 283–301 (1972); J. C. Watkins and R. H. Evans, Ann. Rev, Pharmacol, Toxicol., 21, 165–204 (1981); A. C. Foster and G. Fagg, Brain Res. Rev., 7, 103–164 (1984)]. In addition to these major ion channel-linked receptors, evidence now suggests the presence of metabotropic EAA receptors which directly activate second messenger systems [D. Schoepp, J. Brockaert and F. Soladeczek, In C. Lodge and G. L. Collinridge (eds.) Tr. Pharmacol. Sci., Special Report, "The Pharmacology of Excitatory Amino Acids," Elsevier, Cambridge, U K., 74–81. (1991)]. Furthermore, it is now apparent that the NMDA-mediated ionotropic responses are subject to complex regulatory influences and, that this particular recognition site may exist as a supramolecular entity similar to the GABA/benzodiazepine/barbiturate effector proteins [E. Costa, Neuropsycholpharmacology, 2, 167–174 (1989)].

In general EAA agonists are potent convulsants in animal models. Additionally, AMPA, KA and the endogenous NMDA agonist, quinoline acid (QUIN) and the mixed ionotropic/metabotropic agonist ibotenic acid have been used to produce laboratory models of neurodegenerative disorders [K. Biziere, J. T. Slevin, R. Zaczek, J. S. Collins and J. T. Coyle. In H. Yoshida, Y. Hagihara and S. Ebashi (eds.), "Advances in Pharmacology and Therapeutics," New York: Pergamon 271–276 (1982); R. Schwarcz, E. O. Whetsell and R. M. Mango, Science, 219, 316–318 (1983)]. It has been suggested for some time that a dysfunction in EAA neurotransmission may contribute to the neuropathology associated with the epilepsies and neurodegenerative conditions [B. Meldrum and M. Williams (eds.), "Current and Future Trends in Anticonvulsant Anxiety. and Stroke Therapy, " Liss New York: Wiley, (1990)], The development of selective NMDA antagonists has further expanded the understanding of EAA neurotransmission, physiology and pathophysiology in the mammalian brain. In particular, substantial preclinical evidence is now available suggesting the NMDA receptor antagonists may be useful as anxiolytics, anticonvulsants, antiemetics, antipsychotics or muscle relaxants, and that these compounds may prevent or reduce neuronal damage in instances of cerebral ischemia, hypoxia, hypoglycemia or trauma [R. P. Simon, J. H. Swan, T. Griffiths and B. S. Meldru, Science, 226, 850–852 (1984); D. N. Stephens, B. S. Meldrum, R. Weidman, C. Schneider and M. Grutzner, Psychopharmacology, 90, 166–169 (1986); D. Lodge and G. L. Collinridge (eds.) "The Pharmacology of Excitatory Amino Acids, " Elsevier Trends Journals, Cambridge, U K. (1991);e A. I. Fader, J. A. Ellison and L. J. Noble, Eur. J. Pharmacol., 175, 165–174 (1990)].

Given the broad therapeutic potential of EAA antagonists, it is not surprising that efforts have been initiated to identify antagonist compounds. The advent of potent and selective antagonists of EAAs exemplified by α-amino-ω-phosphonoalkylcarboxylic acids has been provided a point of departure for the pharmacologic intervention of EAA action at their receptors [J. C. Watkins, Can. J. Physiology Pharmacol., 69, 1064–1075 (1991)]. While there has been substantial success in finding competitive and non-competitive antagonists of non-NMDA receptors, there are few reports of potent and selective antagonists of KA or AMPA-type EAA receptors [J. C. Watkins, P. Krogsgaard-Larsen and T. Honore, In D. Lodge and G. L. Collinridge (eds.), "The Pharmacology of Excitatory Amino Acids," Elsevier Trends Journals, Cambridge, U.K., 4–12 (1991); M. J. Sheardown, E. O. Nielson, A. J. Hansen, P. Jacobsen and T. Honore, Science, 247, 571–573 (1990); A. Frasden, J. Drejer and A. Shousboe, J. Neurochem., 53, 297–300 (1989)]. Identification of such antagonists is important since these agents are expected to share many of the potential therapeutic actions of antagonists of NMDA-type EAA receptors.

Other related compounds having NMDA antagonist activity have been reported in Rzeszotarski et al., U.S. Pat. No. 4,657,899. In particular, Rzeszotarski et al. disclose potent and selective EAA neurotransmitter receptor antagonists having the general formula:

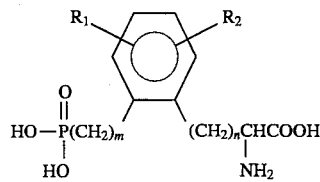

wherein $R_1$ and $R_2$ are the same or different and are selected from the group consisting of hydrogen, lower alkyl, halogen, amino, nitro, trifluoromethyl or cyano, or taken together are —CH=CH—CH=CH—; n and m =0, 1, 2, or 3; and the pharmaceutically acceptable salts and the 2-acetamido-2-carboethoxy esters thereof. Rzeszotarski et al. also disclose specific compounds, including 2-amino-3-[2-(2-phosphonoethyl)phenyl] propanoic acid, 2-amino-3-[2-(3-phosphonopropyl) phenyl] pentanoic acid, 2-amino-5-[2-phosphonomethylphenyl]pentanoic acid, and 2-amino-3-[2-phosphonomethylphenyl]propanoic acid which are disclosed as antagonists of NMDA and show very low binding affinity for kainate receptors; see Table I on column 13. The valuable pharmacological properties of the present new compounds are particularly surprising in view of the compounds disclosed and described in U.S. Pat. No. 4,657,899.

SUMMARY OF THE INVENTION

The present invention provides an excitatory amino acid KA/AMPA acid receptor antagonist compound having the general formula:

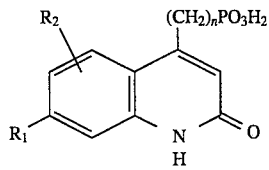

wherein n is 0, 1, 2 or 3; R1 and R2 are selected from the group consisting of hydrogen, halogen, halomethyl, nitro, amino, alkoxy, hydroxyl, hydroxymethyl, C1 to C6 lower alkyl and C7 to C12 higher alkyl, aryl, and aralkyl; and the pharmaceutically acceptable salts thereof.

More particularly, the invention provides a potent and selective excitatory amino acid receptor antagonist having the general formula:

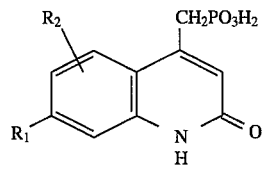

wherein R1 and R2 are selected from the group consisting of hydrogen, halogen, nitro, and C1 to C6 lower alkyl.

Another aspect of the invention involves use of the pharmaceutical compositions for relieving pain, treatment of convulsions or epilepsy, enhancing cognition, treating psychosis, preventing neurodegeneration, treating cerebral ischemia or trauma-induced damage, and treating emesis.

A further aspect of this invention involves a method for antagonizing excitatory amino acid KA and/or AMPA receptors by utilizing a compound having the general formula:

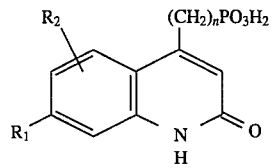

wherein n is 0, 1, 2 or 3; R1 and R2 are selected from the group consisting of hydrogen, halogen, halomethyl, nitro, amino, alkoxy, hydroxyl, hydroxymethyl, C1 to C6 lower alkyl and C7 to C12 higher alkyl, aryl and aralkyl; and the pharmaceutically acceptable salts thereof.

The compounds of the present invention describe a novel class of EAA antagonists in which the phosphonoalkyl moiety has been appended to a heterocyclic ring; specifically, to the 4-position of a substituted quinolin2-one. These compounds have been found to potently and selectively antagonize KA/AMPA neurotransmission, and represent a novel class of such antagonists.

Particularly preferred specific compounds include:
7-Chloro-4-phosphonoethylquinolin-2-one
7-Chloro-4-phosphonomethylquinolin-2-one
7-Iodo-4-phosphonomethylquinolin-2-one
5,7-Dichloro-4-phosphonomethylquinolin-2-one
6,7-Dichloro-4-phosphonomethylquinolin-2-one

DETAILED DESCRIPTION OF THE INVENTION

The structure and formulation of the novel compounds of the invention was the result of an extensive research effort into the antagonism of excitatory amino acid (EAA) neurotransmission with focus on the kainic acid (KA) and AMPA subtypes of EAA receptor.

It is generally accepted that L-glutamic acid (GLU) is the principal excitatory neurotransmitter in the vertebrate central nervous system (CNS). Ion channel-linked or "ionotropic" EAA receptor subtypes include those selectively activated by N-methyl-D-aspartate (NMDA), α-amino-3-hydroxy-5-methyl-4-isoxazole propionic acid (AMPA), and kainic acid (KA). A "metabotropic" GLU receptor coupled to phospholipid metabolism and a putative GLU autoreceptor have also been identified. L-glutamic acid is also believed to have an important physiological role in the functioning of the CNS since a great majority of CNS neurons utilize GLU as their neurotransmitter.

Beyond its involvement in excitatory neurotransmission, GLU has been suggested to play a role in CNS pathologies characterized by heightened neuronal activity or sensitivity, including epilepsy, ischemic or trauma-induced neuronal damage, and certain neurologic and neurodegenerative disorders. Accordingly, the pharmacological manipulation of GLU receptors may be therapeutically useful in the treatment of several CNS disorders and diseases.

The NMDA receptor is the most well-characterized of the GLU receptor subtypes because of the availability of potent and selective antagonists. D-(-)-2-amino-5phosphonopentanoic acid (AP5) and D-(-)-2-amino-7phosphonoheptanoic acid (AP7) were among the first NMDA antagonists identified and act competitively by binding to the GLU recognition site.

Competitive NMDA antagonists have been demonstrated to be effective as anticonvulsant and cerebroprotective agents. A growing body of evidence also suggests that blockade of non-NMDA receptors is useful in the treatment of CNS disorders involving glutamatergic neurotransmission. This latter use has been supported by experiments in which KA-induced seizures have been used as animal models of temporal lobe epilepsy in humans. Another potential therapeutic use for a KA and/or AMPA antagonist in the treatment of neurodegenerative disorders is indicated by the finding that intrastriatal administration of KA produces a pattern of neuronal damage in rats similar to that observed in Huntington's chorea. Non-NMDA receptors have also been implicated in neurologic disorders including Lathyrism, an upper motor neuron disease characterized by spastic paraparesis, and Guam's disease, a form of amyotrophic lateral sclerosis.

In contrast to NMDA receptor antagonists a limited number of KA/AMPA receptor antagonists have been described, the majority of which are weak and relatively non-selective; for this reason, the full characterization of the functional and physiological properties of these receptors has not been realized to date. However, a series of quinoxalidiones were recently identified as potent non-NMDA antagonists. The therapeutic potential of these compounds is illustrated by their ability to protect against EAA agonist-induced cytotoxicity in cultured cortical neurons and clonic seizures in neonatal rats.

The compounds of the present invention have been identified which antagonize KA and AMPA-induced currents in Xenopus oocytes infected with rat brain mRNA. The structure and formulation of the novel compounds of this invention relate specifically to EAA receptors activated by either KA or AMPA for which only a limited number of quinoxalines have been identified as specific antagonists. See Watkins et al. In D. Lodge and G. L. Collinridge (eds.), "The Pharmacology of Excitatory Amino Acids," *Elsevier Trends Journals*, Cambridge U.K., 4–12 (1991).

In a preferred embodiment, the novel compounds of the present invention provide potent antagonists having greater affinity for KA and AMPA receptors and lesser or no affinity for other CNS receptors, rendering the compounds very selective; this would permit one to selectively antagonize one EAA receptor in tissues also containing other EAA receptors. Fewer side effects can be expected as a result of the greater affinity and selectivity of the compounds of the present invention.

The present invention provides an excitatory amino acid KA/AMPA acid receptor antagonist compound having the general formula:

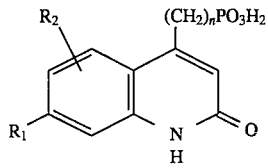

wherein n is 0, 1, 2, or 3; R1 and R2 are selected from the group consisting of hydrogen, halogen, halomethyl, nitro, amino, alkoxy, hydroxyl, hydroxymethyl, C1 to C6 lower alkyl and C7 to C12 higher alkyl, aryl and aralkyl; and the pharmaceutically acceptable salts thereof.

More particularly, the invention provides a potent and selective excitatory amino acid receptor antagonist having the general formula:

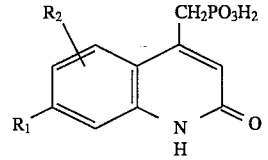

wherein R1 and R2 are selected from the group consisting of hydrogen, halogen, nitro, and C1 to C6 lower alkyl; and the pharmaceutically acceptable salts thereof.

In a preferred aspect of the invention R1 and R2 are not both hydrogen, that is, when one is hydrogen the other is selected from a material other than hydrogen.

Another aspect of the invention involves use of the pharmaceutical compositions for relieving pain, treatment of convulsions or epilepsy, enhancing cognition, treating psychosis, preventing neurodegeneration, treating cerebral ischemia or trauma-induced damage, and treating emesis.

A further aspect of this invention involves a method for antagonizing excitatory amino acid KA and/or AMPA receptors by utilizing a compound having the general formula:

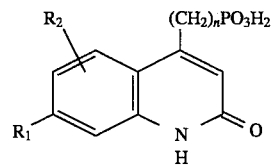

wherein n is 0, 1, 2 or 3; R1 and R2 are selected from the group consisting of hydrogen, halogen, halomethyl, nitro, amino, alkoxy, hydroxyl, hydroxymethyl, C1 to C6 lower alkyl and C7 to C12 higher alkyl, aryl and aralkyl; and the pharmaceutically acceptable salts thereof.

Particularly preferred specific compounds include:
7-Chloro-4-phosphonomethylquinolin-2-one
7-Iodo-4-phosphonomethylquinolin-2-one
5,7 Dichloro-4-phosphonomethylquinolin-2-one
6,7 Dichloro-4-phosphonomethylquinolin-2-one As used in the specification and claims, "alkyl" is a paraffinic hydrocarbon group which may be derived from an alkane by dropping one hydrogen from the formula, such as methyl, ethyl, propyl, isopropyl, butyl, and so forth.

"Halogen" includes bromo, fluoro, chloro and iodo; "halomethyl" includes mono-, di-, and tri-halo groups including trifluoromethyl; amino compounds include amine ($NH_2$) as well as substituted amino groups comprising alkyls of one through six carbons; "aryl" is an aromatic ring compounds such as benzene, phenyl, naphthyl and substituted forms thereof; "aralkyl" is an aryl being attached through an alkyl chain, straight or branched, of from one through six carbons, such as a phenylpropyl group.

Abbreviations used in this specification have the following meanings: MCPBA is 3-chloroperoxybenzoic acid (Cl $C_6H_4CO_3H$), THF is tetrahydrofuran, MsCl is methanesulfonyl chloride ($CH_3SO_2Cl$), TBAH is tetrabutylammonium hydrogen sulfate ($[CH_3(CH_2)_3]NHSO_4$), NBS is N-bromosuccinimide, TMS is trimethylsilyl ($Si(CH_3)$), GLU is glutamate, CNQX is 6-cyano-7-nitroquionoxaline-2,3-dione, nd means not determined, and TLC is thin layer chromatography.

The preparation of pharmaceutically acceptable salts of compounds of the present invention may be accomplished by a variety of methods known to those skilled in the art of synthetic organic chemistry. Appropriate pharmaceutically acceptable salts within the scope of the invention are those derived from mineral acids such as hydrochloric acid, phosphoric acid, nitric acid and sulfuric acid; and organic acids such as tartaric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluenesulfonate, and the like, respectively or those derived from bases such as suitable organic and inorganic bases. Examples of suitable inorganic bases for the formation of salts of compounds of this invention include the hydroxides, carbontates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methyl-glucosamine; N-methylglucamine; L-glutamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.*, 66 (1):1–19 (1977).

The preparation of the compounds for administration in pharmaceutical preparations may be accomplished in a variety of ways well known to those skilled in the art of pharmacy. In parenteral administration of the novel compounds and compositions of the invention the compounds may be formulated in aqueous infection solutions which may contain antioxidants, buffers, bacteriostats, and other conventional pharmaceutical excipients. Extemporaneous injection solutions may be prepared from sterile pills, granules or tablets which may contain diluents, dispersing and surface active agents, binders, and lubricants as well as other pharmaceutical processing aids.

In the case of oral administration, fine powders or granules of the compounds may be formulated with diluents, and dispersing and surface active agents. They may also be prepared in water or in a syrup, in capsules or cachets, in the dry state or in a non-aqeous suspension, where a suspending agent may be included. The compounds may also be administered in a tablet form along with optional binders and lubricants, or in a suspension in water or syrup, or an oil or in a water/oil emulsion and may include flavoring, preserving, suspending, thickening and emulsifying agents. The granules or tablets from oral administration may be coated and other pharmaceutically acceptable agents and formulations may be utilized, which are well known to those of ordinary skill in the art.

The following examples are illustrative of preferred embodiments of the invention and are not intended to be construed as limiting the invention thereto. All percentages are based on weight of the final formulation unless otherwise indicated and the weight of all formulations totals 100% by weight.

The novel compounds of the invention may readily be prepared by the following synthetic routes:

SCHEME I

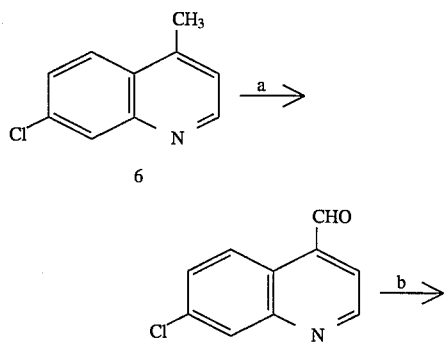

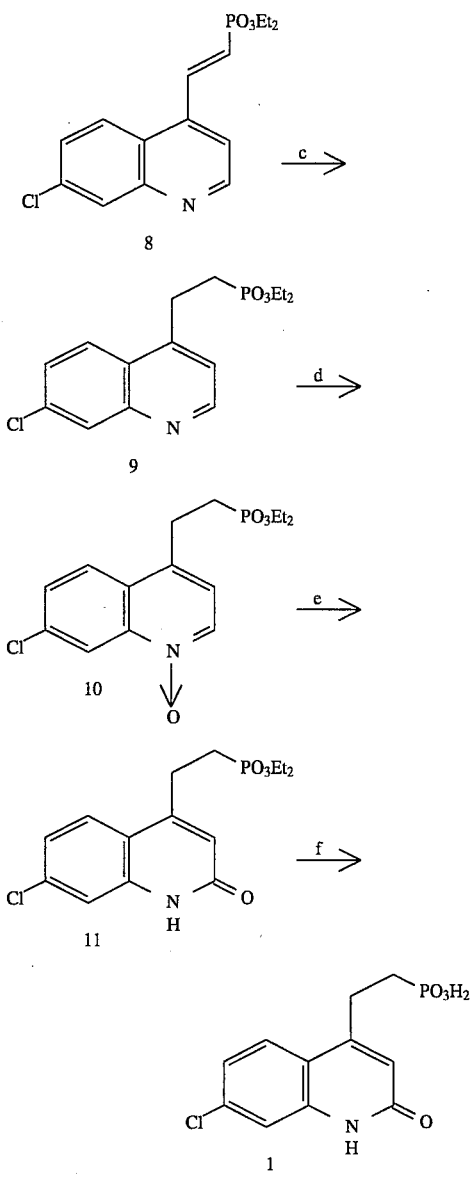

a) SeO₂, dioxane/H₂O
b) Sodio tetraethylmethylene bisphosphonate, THF, 0° C.
c) H₂, 5% Pd/C
d) MCPBA, CHCl₃
e) MsCl, NaOH, TBAH, phase transfer conditions
f) 6N HCl

SCHEME II

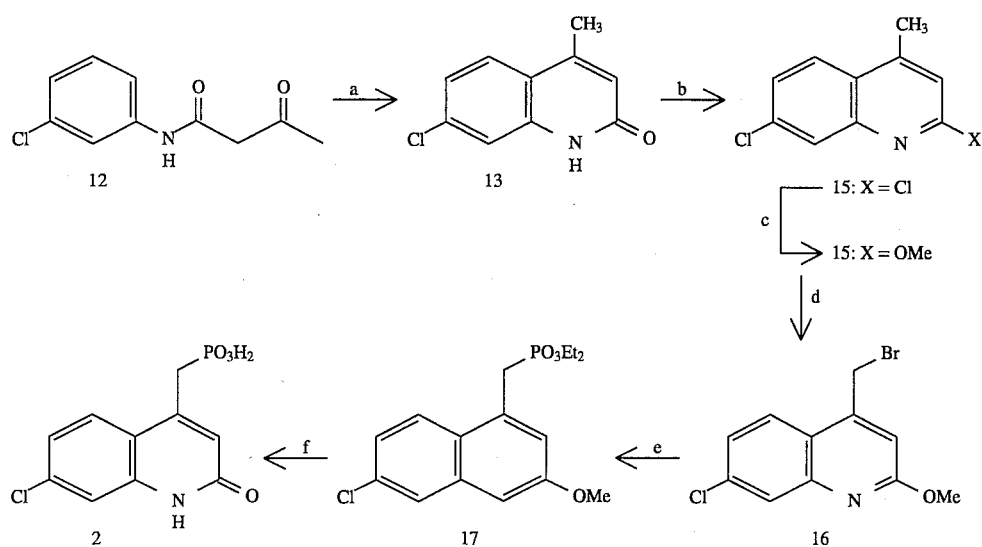

a) Con. H$_2$SO$_4$, 120° C., 1 hr
b) POCl$_3$, reflux, 2 hrs
c) NaOMe/MeOH, reflux, overnight
d) NBS, CCl$_4$ hv;
e) P(OEt)$_3$, reflux, overnight
f) TMS bromide, reflux overnight, then 6N HCl

SCHEME III

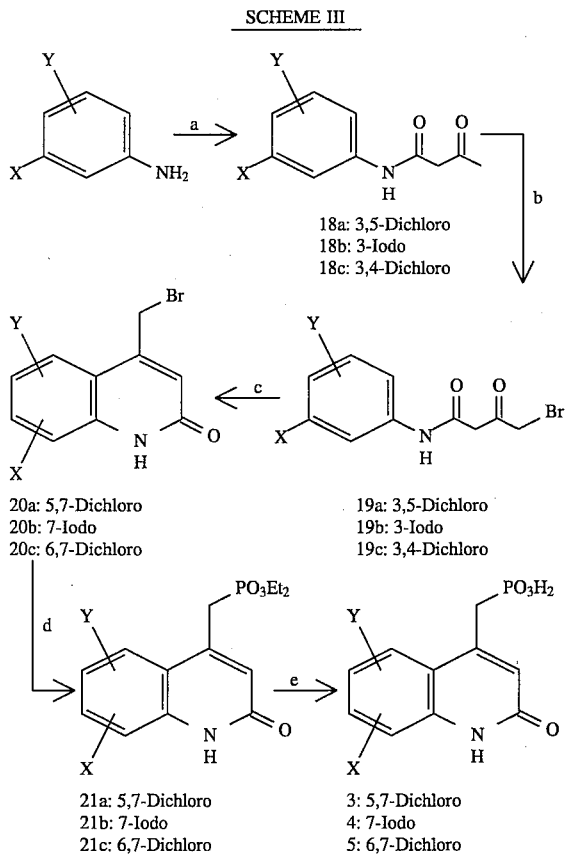

20a: 5,7-Dichloro
20b: 7-Iodo
20c: 6,7-Dichloro

19a: 3,5-Dichloro
19b: 3-Iodo
19c: 3,4-Dichloro

21a: 5,7-Dichloro
21b: 7-Iodo
21c: 6,7-Dichloro

3: 5,7-Dichloro
4: 7-Iodo
5: 6,7-Dichloro a) Diketene, toluene, reflux 2 hrs
b) Br$_2$, CHCl$_3$
c) Con. H$_2$SO$_4$, 120° C., 1 hr -continued
SCHEME III d) P(OEt)$_3$, reflux overnight
e) 6N HCl, reflux overnight

PREPARATION OF EXAMPLE 1

7-Chloroquinoline-4-carboxaldehyde (7)

Selenium dioxide (4.52g; 40.3mmol) in a mixture of 25ml of dioxane and 6ml of water was added in a dropwise fashion to 7-chlorolepidine (6; 6.50g; 36.6mmol) in 25ml of dioxane to 65°–75° C. The temperature was raised to 85° C. and maintained there with stirring for 6 hours. After cooling, the mixture was filtered through Celite™ and concentrated. The crude material was purified on a flash column, eluting with 10% ethyl acetate/hexane to obtain 5.24g (74%) of aldehyde 7 as a yellow solid. $^1$H NMR (CDCl$_3$): δ7.68 (d, 1H); 7.79 (d, 1H); 8.19 (d, 1H); 9.01 (dd, 1H); 9.21 (m, 1H); 10.45 (s, 1H). IR (KBr): 1702, 1499, 1216, 1041, 900, 653 cm$^{-1}$.

7-Chloro-4-[(diethoxyphosphinyl)ethenyl]quinoline (8)

To a stirred suspension of sodium hydride (978 mg of an 80% dispersion; 32.6 mmol) in a 60 ml of THF at 0° C. was added 7.83 g (32.6 mmol) of tetraethylmethylenebisphosphonate in 20 ml of THF. After stirring at room temperature (about 24° C.) for 1 hour, the solution was cooled to –78° C. and aldehyde 7 (5.20 g; 27.15 mmol) in 30 ml of THF was added dropwise. The reaction was stirred at –78° C. for 30 minutes before returning to room temperature. After stirring for an additional 2 hours, the reaction was quenched with 10 ml of 10% NH$_4$Cl. The product was extracted into 2 ×10 ml of ethyl acetate; the organic. layers were combined, washed with 2 ×10 ml of brine and dried over MgSO$_4$. The solvent was evaporated and the crude product purified on a silica gel column, eluting with 2% methanol/ethyl acetate to obtain 7.6 g (86%) of the product as a syrup. $^1$H NMR (CDCl$_3$): δ1.409 (t, 3H); 4.20 (q, 2H); 6.56 (t, 1H, J=17 Hz); 7.58 (d, 1H, J=4.5 Hz); 7.57 (dd, 1H, J=2 Hz, 9 Hz); 8.07–8.23 (m, 2H); 8.94 (d, 1H, J=4.5 Hz). IR (neat): 3492, 2983, 1604, 1584, 1494, 1244, 1036, 964, 851, 787 cm$^{-1}$.

7-Chloro-4-[2'- (diethoxyphosphinyl) ethyl quinoline (9)

A mixture of vinyl phosphonate 8 (7.6 g; 23.35 mmol) and 5% palladium on carbon (760 mg) in 50 ml of ethanol was hydrogenated at 50 psi of hydrogen for 2 hours. The mixture was filtered through Celite™ and concentrated. Thin layer chromatography indicated several products present. The crude residue was purified through a flash column (2% methanol/CH$_2$Cl$_2$) to deliver 2.8 g (37%) of phosphonoethyl compound 9. $^1$H NMR (CDCl$_3$): δ1.34 (t, 3H); 2.14 (m, @H); 3.36 (m, 2H); 4.13 (q, 2H); 7.27 (d, 1H, J=3.6 Hz); 7.55 (dd, 1H, J=2.2, 9 Hz); 7.98 (d, 1H, J=9 Hz); 8.12 (d, 1H, J=2.2 Hz); 8.82 (d, 1H, J=3.6 Hz). IR (CDCl$_3$): 2985, 1792, 1607, 1499, 1391, 1242, 907, 732 cm$^1$.

7-Chloro-4-[2'diethoxyphosphinyl)ethyl]quinoline-N-oxide (10)

A solution of 80% MCPBA (45 mg; 0.67 mmol) in 3 ml of CHCl$_3$ was added to quinoline 9 (200 mg; 0.61 mmol) in 2 ml of CHCl$_3$. After stirring at room temperature for 4 hours, an additional 53 mg of MCPBA was added and stirring was continued overnight. The reaction mixture was washed with 2 ×1 ml of saturated Na$_2$CO$_3$ and 2 ×1 ml of brine, dried (MgSO$_4$) and freed of solvent. The crude product was recrystallized from CH$_2$Cl$_2$/methy t-butyl ether to obtain 180 mg (86%) of the N-oxide as a crystalline white solid, mp 117° C. $^1$H NMR (CDCl$_3$): δ1.34 (t, 3H); 2.13 (m, 2H); 3.32 (m, 2H); 4.14 (q, 2H); 7.18 (d, 1H, J=6 Hz); 7.65 (dd, 1H, J=2, 9 Hz); 7.98 (d, 1H, J=9 Hz); 8.47 (d, 1H, J=6 Hz) 8.85 (d, 1H, J=2 Hz). IR (KBr): 3091, 2980, 2908, 1566, 1430, 1240, 1024 cm$^{-1}$.

7-Chloro-4- [2'- (diethoxyphosphinyl) ethyl ]quinolin-2-one (11)

A solution on N-oxide 10 (400 mg; 1.16 mmol) and methanesulfonyl chloride (266 mg; 2.32 mmol) in 4 ml of CH$_2$Cl$_2$ was added to a two phase mixture of water (2 ml) and CH$_2$Cl$_2$ (2ml) containing 232 mg of NaOH and 472 mg of tetrabutylammonium hydrogen sulfate. This mixture was stirred gently overnight. The layers were washed with brine, dried over MgSO$_4$, and concentrated. The residue was purified through a flash column, eluting with 5% methanol/CH$_2$Cl$_2$, to obtain 260 mg (65%) of 10 as a yellowish foam. $^1$H NMR (CDC$_l$3): δ1.37 (t, 3H); 2.13 (m, 2H); 3.15 (m, 2H); 4.18 (q, 2H); 6.62 (s, 1H); 7.22 (dd, 1H, J=1.5, 8.5 Hz); 7.50 (d, 1H, J=1.5 Hz); 7.66 (d, 1H, J=8.5 Hz). IR (CHCl$_3$): 3155, 1792, 1661, 1471, 1381, 1095, 905, 733, 468cm$^{-1}$.

7-Chloro-4-phosphonethylquinolin-2-one (1)

A solution of phosphonate 11(250 mg; 0.73 mmol) in 6N HCl (9 ml) was refluxed overnight. The white precipitate which formed was collected and washed with 3 ×2 ml cold H$_2$O, 2×2 ml methanol, and 2×3 ml of ether, and dried in a vacuum desiccator. The product was obtained as a white solid, mp 303°–304° C. (180 mg; 86%). 1H NMR (D20): δ1.67–1.78 (m, 2H); 3.00–3.07 (m, 2H); 6.55 (s, 1H); 7.18 (d, 1H); 7.42 (s, 1H); 7.85 (d, 1H). IR (KBr): 3062, 2944, 2895, 1675, 1560, 1507, 1458, 1352, 1187, 1070, 877, 766 cm$^{-1}$. Anal. Calc'd. for C$_{11}$H$_{11}$NO$_4$PCl : C, 45.91; H, 3.86: N, 4.87. Found: C, 45.77; H, 3.89; N, 4.82.

PREPARATION OF EXAMPLE 2

7-chloro-4-methylquinolin-2-one (13)

A solution of diketene (22.96 g; 0.33 mol) in 120 ml of toluene was added dropwise to a warmed (80° C.) solution of 3-chloraniline (33.82 g; 0.27 mol) in 25 ml of toluene. The resulting mixture was heated to reflux for 5 hours. The orange crystalline material which formed was collected and washed with cold hexane. After drying under vacuum, 40.60 g (72%) of acetoacetanilide 12 was obtained, which was taken on directly to the cyclization step. A solution of this product in concentrated H$_2$SO$_4$ (300 ml) was heated to 120° C. for 1 hour, then cooled and poured into ice-water. The yellowish precipitate was collected and washed with ice-cold water and brine and dried under vacuum to obtain 33 g (90%) of 13. $^1$H NMR (DMSO-d$^6$): δ2.33 (s, 3H); 6.50 (s, 1H); 7.30 (dd, 1H, J=2 Hz, 8.6 Hz); 7.41 (d, 1H, J=2 Hz); 7.80 (d, 1H, J=86 Hz); 11.70 (br, 1H). IR (KBr): 2797, 1691, 1401, 1383, 923 cm$^{-1}$.

2,7-Dichloro-4-methylquinoline (14)

A solution of quinolone 13 (10 g; 51.6mmol) in 90 ml of POCl$_3$ was refluxed for 2 hours. After cooling, the mixture was poured into 300 g ice-water and neutralized with NH$_4$OH. The resultant precipitate was filtered off and washed with cold H$_2$O. The crude product was recrystallized from 95% ethanol to obtain 8.95 g (72%) of 14. $^1$H NMR (CDCl$_3$): δ2.71 (s, 3H); 7.28 (d, 1H); 7.55 (d, 1H); 7.92 (d, 1H); 8.08 (d, 1H).

7-Chloro-2-methoxy-4-methylquinoline (15)

2-Chloroquinoline 14 (7.0 g; 32.8 mmol) was added to a solution of sodium methoxide in methanol generated from 1.08 g (36.1 mmol) of 80% sodium hydride in 80 ml of methanol. The resulting mixture was refluxed overnight. It was filtered while still hot to remove undissolved matter. The product crystallized from the methanol upon cooling to deliver 6.1 g (70%) of 15 as a white solid. $^1$H NMR (CDCl$_3$);: δ2.62 (s, 3H); 4.10 (s, 3H); 6.78 (s, 1H); 7.38 (d, 1H); 7.81 (d, 1H); 7.93 (d, 1H).

7-Chloro-4-bromomethyl-2-methoxyquinoline (16)

N-bromosuccinimide (6.40 g; 36 mmol) was added to a solution of quinoline 15 (5.0g; 24 mmol) in 50 ml of CCl$_4$. After irradiation with a 60W bulb for 1 hour, an additional 2 g of N-bromosuccinimide was added and irradiation was continued for 30 minutes. After cooling, the solution was filtered and the filtrate was concentrated under reduced pressure. An initial purification on a silica gel column, eluting with 20% ethyl acetate in hexane, gave 720 mg of pure monobromide plus 5.5 g of a mixture containing monobromide 16 together with a minor amount of dibromide. $^1$H NMR (CDC$_l$3): δ4.05 (s, 3H); 4.71 (s, 2H); 6.94 (s, 1H); 7.42 (dd, 1H, J=2, 9 Hz); 7.90 (m, 4H). IR (KBr): 2949, 2360, 1610, 1407, 1468, 1345, 1198, 1028, 825, 694 cm$^{-1}$.

7-Chloro-4-(diethoxyphosphinyl)methyl-2-methoxyquinoline (17)

A solution of bromide 16 (470 mg; 1.64 mmol) in triethylphosphite (4 ml) was refluxed overnight. The excess triethylphosphite was removed under vacuum and the residue was purified through a silica gel column eluting with 3% methanol in CH$_2$Cl$_2$ to obtain 300 mg (53%) of product as a white crystalline solid, mp 93.5°–94.5° C. $^1$H NMR (CDCl$_3$): δ1.21 (t, 3H); 3.50 (d, 2H, J=23 Hz); 4.04 (q, 2H); 6.88 (d, 1H, J=4 Hz); 7.36 (dd, 1H, J=2, 9 Hz); 7.88 (dd, 1H, J=2, 9 Hz). IR (KBr): 2978, 23589, 1607, 1383, 1344, 1247, 1046, 1018, 964, 789 cm$^{-1}$. 7-Chloro-4-phosphonomethylquinolin-2-one (2)

A solution of diethylphosphonate 17 (160 mg; 0.57 mmol) in trimethylsilylbromide (4ml) was refluxed overnight. The solvent/reagent was removed in vacuo and the residue was dissolved in 3 ml of 1N NaOH and washed with 2 ×1 ml of ether. The aqueous layer was acidified to pH 1 with 6N HCl and the precipitate which was formed was collected and washed with cold water, methanol and ether. The product was obtained as a white solid, mp 186° C. (dec) (80mg; 60%). $^1$H NMR (D20): δ3.06 (d, 2H, J =20.3 Hz); 6.54 (d, 1H, J=3.32 Hz); 7.12 (dd, 1H, J=2.03, 8.89 Hz); 7.36 (d, 1H, J=2.03 Hz); 7.89 (d, 1H, j =8.80 Hz). IR (KBr): 2931, 2828, 2360, 2309, 1658, 1643, 1532, 1406, 1224, 1147, 1093 cm$^{-1}$. Anal. Calc'd for $C_{10}H_9NO_4ClP$: C, 43.89; H, 3.32; N, 5.12. Found: C, 43.69; H, 3.41; N, 5.02.

PREPARATION OF EXAMPLES 3 TO 5

3,5-Dichloracetoacetanilide (18a)

Diketene (39.7 g; 463 mmol) in 120 ml of toluene was added in a dropwise fashion to a solution of 3,5-dichloroaniline (62.2 g; 380 mmol) in 250 of toluene at 80° C. After the addition was complete, the mixture was refluxed for 5 hours. The mixture was cooled and reduced to half its volume under reduced pressure, at which point the crude product precipitated out of solution. The product was purified by recrystallizing from ether/hexane to obtain 64.7 g (57%) of crystalline white solid, mp 69°– 70° C.

$^1$H NMR (CDCl$_3$): δ2.05 (s, 3H); 3.60 (s, 2H); 7.1–(s, 1H); 7.52 (s, 2H), 10.39 (br, 1H). IR (KBr): 3281, 3178, 1712, 1648, 1589, 1543, 1445, 1414, 1360, 1196, 854, 802 cm$^{-1}$.

3-Iodacetoacetanilide (18b, mp 106°–107° C.) was prepared in the same manner as (18a). $^1$H NMR (CDCl$_3$): δ2.33 (s, 3H); 3.60 (s, 2H); 7.05 (t, 1H, J=8 Hz); 7.45 (d, 1H, J=8 Hz); 7.51 (d, 1H, j+8 Hz), 7.97 (s, 1H), 9.43 (br, 1H). IR (KBr): 3286, 1712, 1661, 1581, 1545, 1476, 1417, 1337, 1162, 781, 766 cm$^{-1}$.

3,4 Dichloroacetanilide (18c, mp 88.5°–89.5° C.; 55%) was prepared in the same manner as (18a). $^1$H NMR (CDCl$_3$): d 2.33 (s, 3H); 3.60 (s, 2H); 7.36 (m, 2H); 7.80 (s, 1H); 9.38 (br, 1H). IR 3289, 1720, 1666, 1599, 1543, 1476, 1376, 1160, 1136, 879, 733 cm$^{-1}$.

3,5 Dicholoro-ω-bromoacetoacetanilide (19a)

A solution of bromine (3.27 g; 20.4 mmol) in 5 ml of CHCl$_3$ was added to a solution of the acetoacetanilide (5.0 g; 20.4 mmol) in 15 ml of CHCl$_3$ in a dropwise fashion. The mixture was heated to 70° C. for 2 hours, then cooled and the precipitate collected and washed with methylene chloride and hexane. This crude product was purified through silica gel chromatography, eluting with 10% ethyl acetate/hexane, to obtain 1.35 g(20%) of a yellowish solid, mp 137° C. (dec.). $^1$H NMR (CDCl$_3$); δ3.85 (s, 2H); 4.06 (s, 2H); 7.13 (s, 1H); 7.47 (m, 2H); 8.88 (br, 1H). IR (KBr): 3283, 1731, 1663, 1586, 1540, 1417, 1327, 1049, 851, 669 cm$^{-1}$.

3-Iodo (19b, mp 102.5°–103.5° C.; 27%) was prepared in the same manner as (19a). $^1$H NMR (CDCl$_3$): δ3.83 (s, 2H); 4.06 (s, 2H); 7.03 (m, 1H); 7.46 (m, 2H); 7.92 (s, 1H); 8.67 (br, 1H). IR (KBr): 3250, 1738, 1651, 1576, 1538, 1400, 1329, 1190, 1080, 784, 686 cm$^{-1}$.

3,4 Dichloro (19c, 40%) was prepared in the same manner as (19a).

$^1$H NMR (CDCl$_3$): δ3.84 (s, 2H); 4.12 (s, 2H); 7.37 (m, 2H); 7.78 (s, 1H); 8.87 (br, 1H). IR (KBr): 3296, 1589, 1532, 1476, 1131, 1028, 812 cm$^{-1}$.

4-Bromomethyl-5,7-dichloroquinolin-2-one (20a)

A mixture of bromoacetoacetanilide 19a (1.33 g; 4.1 mmol) in 5 ml of con. H$_2$SO$_4$ was heated to 120°C. for 1 hour, then cooled and poured into 20 ml of ice water. The precipitate was collected and washed with cold water and ether. After drying in a vacuum desiccator there was obtained 800 mg (64%) of the product as a light brown solid, mp 259°–260° C. (dec). $^1$H NMR (DMSO-d$^6$): δ5.08 (s, 2H); 6.85 (s, 1H); 7.36 (s, 1H); 7.43 (s, 1H); 12.16 (br, 1H). IR (KBr): 2834, 1668, 1599, 1399, 854, 730 cm$^{-1}$.

4-Bromomethyl-7-iodoquinolin-2-one (20b, mp 298° C.[dec], 96% was prepared in the same manner as (20a).

$^1$H NMR (DMSO-d$^6$): δ4.87 (s, 2H); 6.76 (s, 1H); 7.59 (m, 2H); 7.70 (s, 1H); 11.83 (br, 1H). IR (KBr): 2823, 1658, 1602, 1543, 1412, 887, 877 cm$^{-1}$.

4-Bromomethyl-6,7-dichloroquinolin-2-one (20c, mp 299°–301° C., 45%) was prepared in the same manner as (20a).

$^1$H NMR (DMSO-d$^6$): δ4.87 (s, 2H); 6.76 (s, 1H); 7.46 (s, 1H); 8.03 (s, 1H). IR (KBr): 2867, 2800, 1666, 1543, 1476, 1412, 1135, 895 cm$^{-1}$.

5,7-Dichloro-4-(diethoxyphosphinyl)methylquinolin-2-one (21a)

A mixture of bromomethylquinoline 20a (580 mg; 1.90 mmol) in triethylphosphite (6 ml) was refluxed overnight. The formed precipitate was filtered and washed with ether. The crude material was recrystallized from acetone to deliver 540 mg of product (78%), mp 210°–202° C.

$^1$H NMR (DMSO-d$^6$): δ1.11 (t, 6H); 3.32 (s, 1H); 3.97 (m, 5H); 6.53 (d, 1H, J=4 Hz); 7.33 (d, 1H, J=2 Hz); 7.36 (d, 1H, J=2 Hz); 12.05 (br, 1H). IR (KBr): 2985, 1682, 1589, 1234, 1059, 1034, 1023, 964 cm$^{-1}$.

7-Iodo-4-(diethoxyphosphinyl)methylquinolin-2-one (21b, mp 196.5°–197.5° C. 55%) was prepared in the same manner as (21a).

$^1$H NMR (DMSO-d$^6$): δ1.03 (t, 3H); 3.57 (d, 2H, J =22 Hz); 4.01 (q, 4H); 6.55 (d, 1H); 7.46 (d, 1H); 7.61 (d, 1H); 7.69 (s, 1H); 11.75 (br, 1H). IR (KBr): 2980, 1661, 1260, 1028, 872 cm$^{-1}$.

4-(Diethoxyphosphinyl)methyl-6,7-dichloroquinolin-2-one (21c, mp 219°–222° C.; 38%) was prepared in the same manner as (21a). $^1$H NMR (CDCl$_3$): δ1.25 (t, 6H); 3.37 (d, 2H, J =23 Hz); 4.12 (q, 4H); 6.72 (d, 1H); 7.56 (s, 1H); 7.91 (s, 1H). IR (Kbr): 2980, 1664, 1476, 1409, 1247, 1031 cm$^{-1}$.

5,7-Dichloro-4-phosphonomethylquinolin-2-one (3)

A solution of the phosphonate (200 mg; 0.55 mmol) in 6N HCl (5 ml) was refluxed overnight. The solvent was removed under reduced pressure and the residue was dissolved in 3 ml 1N NaOH and washed with 3×1 ml ether. The aqueous layer was acidified with 3N HCl, with cooling, and the resultant precipitate was collected, washed with cold water, methanol, and ether, and dried (NMR (D$_2$O): δ3.59 (d, 2H, J=20.6 Hz); 6.55 (d, 1H, J=4.5 Hz); 7.12 (d, 1H, J=2 Hz); 7.25 (d, 1H, J=2 Hz). IR (KBr): 2926, 2317, 1656, 1594, 1520, 1450, 1394, 1198, 1003, 938, 728 cm$^{-1}$. Anal. Calc'd for $C_{10}H_8NO_4Cl_2P$: C, 38.99; H, 2.62; N, 4.55. Found: C, 38.90; H, 2.66; N, 4.53.

7-Iodo-4-phosphonomethylquinolin-2-one (4, mp 239°–331° C.; 60%) was prepared in the same manner as (3). $^1$H NMR (D$_2$O ): δ2.97 (d, 2H, J=20.2 Hz); 6.49 (d, 1H, J=3 Hz); 7.34 (d, 1H, J=8.7 Hz); 7.54 (d, 1H, J=8.7 Hz); 7.69 (s, 1H). IR (KBr): 2924, 2327, 1643, 1525, 1448, 1365, 1270, 1178, 1005 cm$^{-1}$. Anal. Calc'd For $C_{10}H_9NO_4IP$: C, 32.90; H, 2.48; N, 3.84. Found; C, 32.84: H, 2.52; N, 3.80.

6,7-Dichloro-4-phosphonomethylquinolin-2-one (5, mp 213°–218° C. [dec]; 68%) was prepared in the same manner as (3). $^1$H NMR (D20): δ2.80 (d, 2H, J=20.1 Hz); 6.37 (s, 1H); 7.26 (s, 11H); 7.71 (s, 1H). IR (KBr): 2900, 1646, 1406, 1234, 1005, 879 cm$^{-1}$. Anal. Calc'd for $C_{10}H_8NO_4Cl_2P$–0.05 H$_2$O: C, 37.88; H, 2.86; N, 4.42. Found: C, 37.98; H, 2.85; N, 4.41.

Inhibition of EAA-Induced Currents in Xenopus Oocytes

Defolliculated oocytes obtained from Xenopus laevis females were injected with 30–75 ng of poly (A+) mRNA obtained from 21-day old male Sprague-Dawley rats. Oocytes were placed individually in 100 ml of antibiotic-supplemented modified Barthes solution (MBS, containing in mM: NaCl, 88; KCl 1.0; NaHCO$_3$, 2.4 HEPES, 10; MgSO$_4$ 0.82; Ca(NO$_3$)$_2$, 0.33) in 96-well sterile plates and cultured for 48–120 hours prior to experimentation. Oocytes were inspected every 24 hours at which time the bathing solution is replaced with fresh MBS.

For electrophysiological studies, oocytes were positioned in a small recording chamber (500 ml) and superfused with antibiotic free MBS supplemented with CaCl$_2$(final concentration=1.4 mM). Oocytes are impaled with a single glass microelectrode, voltage clamped at –60 to –70 mV, and perfused by gravity feed at a rate of 3–5 ml/min at room temperature. Drugs are dissolved in the perfusate (pH adjusted to 7.3–7.4) and perfused for 1–2 min or until the response has reached a plateau, followed by a 4 min perfusion in the absence of drug(s). Antagonists are coperfused with agonists. MBS used in NMDA assays is prepared from "glycine-free" deionized water.

Potencies to inhibit kainic acid-, AMPA- and NMDA/glycine-induced currents are determined from concentration-response curves. IC$_{50}$ values are converted to K$_i$ values for comparison purposes using the Cheng-Prusoff equation. In Table I, only KA induced currents were looked at; no AMPA responses were evaluated for these compounds. The data indicate the ability of these compounds to block KA induced functional responses. The data in Table II indicate that the compounds 1–5 have significant affinity for CNQX-labeled non-NMDA receptors and that this affinity parallels their ability to block KA induced responses. The compounds vary in their selectivity for NMDA vs non-NMDA receptors; Compounds 1, 3, and 5 are quite selective, while compounds 2 and 4 are not very selective.

Several other related compounds were tested but found to be essentially inactive. These compounds include 5,7-Dichloro-4-(diethoxyphosphinyl)methylquinolin-2-one (21a),
2-Carboxy-7-chloro-4-phosphonethylquinoline (22),

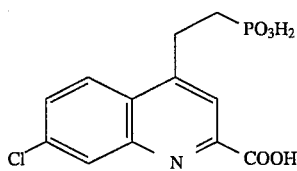

2-Carboxy-7-chloro-4-phosphonomethylquinoline (23),

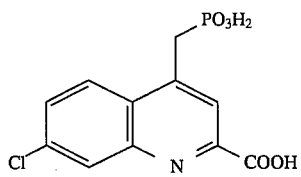

7-Chloro-4-phosphonoquinolin-2-one (24)

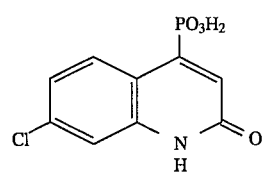

7-Chloro-8-nitro-4-phosphonomethylquinolin-2-one (25),

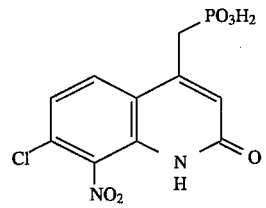

and 6-Chloro-5-nitro-4-phosphonomethylquinolin-2-one (26).

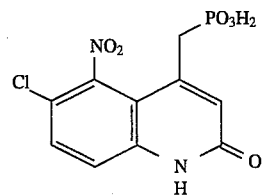

Inhibition of EAA Receptor Ligand binding

Binding assays for the displacement of [$^3$H]AMPA were performed as described by Murphy et al. *(Neurochemical Reseach.* 12: 775–781 [1987]). KA binding assays were performed as described by London et al *(Molecular Pharmacology.* 15:492–505 [1979]); strychnine insensitive glycine binding was evaluated by the method of Snell et al *(European Journal of Pharmacology.* 156: 105–110 [1988].

The results are set forth in Tables I and II.

The invention being thus described, it will be obvious that the same may be varied in many ways. Such variations are not to be regarded as a departure from the spirit and scope of the invention and all such modifications are intended to be included within the scope of the claims.

TABLE I

Potencies of example compounds to inhibit KA-induced currents in rat brain mRNA-injected Xenopus oocytes:

| Example | K$_i$ (µM) |
|---|---|
| 1 | 51 |
| 2 | 32 |
| 3 | 18.2 |
| 4 | 15.6 |
| 5 | 9.6 |
| 21a | 480 |
| 22 | 450 |
| 23 | 129 |
| 24 | >>100 |
| 25 | 379 |
| 36 | >300 |

TABLE II

Inhibition of EAA Receptor Ligand Binding Receptor Potency (K$_i$, µM)

| Example | GLU | CNOX | Glycine |
|---|---|---|---|
| 1 | 600 | 91 | 231 |
| 2 | 30 | 59 | 10 |
| 3 | >100 | 38 | 28 |
| 4 | 35 | 26 | 29 |
| 5 | >100 | 15 | 79 |
| 21a | | >100 | 103 |
| 22 | >100 | 384 | >1000 |

TABLE II-continued

| | Inhibition of EAA Receptor Ligand Binding Receptor Potency ($K_i$, μM) | | |
|---|---|---|---|
| Example | GLU | CNOX | Glycine |
| 23 | | 64 | 68 |
| 24 | >300 | nd | >1000 |
| 25 | >1000 | 300 | >1000 |
| 26 | >1000 | >1000 | >1000 |

What is claimed is:

1. A method for treating a mammal in need thereof with an excitatory amino acid inhibitory compound, comprising the step of administering an effective amount of the following compound:

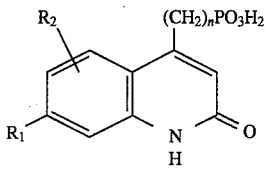

wherein n is 1, 2 or 3 ; $R_1$ and $R_2$ are independently selected from the group consisting of hydrogen, halogen, halomethyl, nitro, amino alkoxy, hydroxyl, hydroxymethyl, $C_1$ to $C_6$ lower alkyl and $C_7$ to $C_{12}$ higher alkyl, aryl and aralkyl, or the pharmaceutically acceptable salts thereof, except $R_1$ and $R_2$ are not nitro and chloro when n is 1.

2. A pharmaceutical composition for relieving pain and treating convulsions, cerebral ischemic damage, and emesis, which comprises: an effective amount of a compound having the formula:

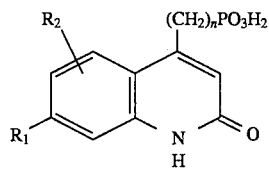

wherein n is 1, 2 or 3; $R_1$ and $R_2$ are independently selected from the group consisting of hydrogen, halogen, halomethyl, nitro, amino alkoxy, hydroxyl, hydroxymethyl, $C_1$ to $C_6$ lower alkyl and $C_7$ to $C_{12}$ higher alkyl, aryl and aralkyl, or the pharmaceutically acceptable salts thereof, except $R_1$ and $R_2$ not nitro and chloro when n is 1; and a pharmaceutically acceptable carrier.

3. A method for relieving pain in a mammal comprising administering an effective amount of a compound of claim 1 to a mammal.

4. A method for treatment of convulsions or epilepsy in a mammal comprising administering an effective amount of a compound of claim 1.

5. A method for treating cerebral ischemic damage in a mammal comprising administering an effective amount of a compound of claim 1.

6. A method for treating emesis in a mammal comprising administering an effective amount of a compound of claim 1.

* * * * *